(12) United States Patent
Izumida et al.

(10) Patent No.: US 8,883,968 B2
(45) Date of Patent: Nov. 11, 2014

(54) METHOD FOR PRODUCING SURFACTIN AND SALT THEREOF

(75) Inventors: Masashi Izumida, Takasago (JP); Hiroaki Kawasaki, Takasago (JP); Tadashi Moroshima, Takasago (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 13/876,734

(22) PCT Filed: Sep. 30, 2011

(86) PCT No.: PCT/JP2011/072578
§ 371 (c)(1),
(2), (4) Date: Mar. 28, 2013

(87) PCT Pub. No.: WO2012/043800
PCT Pub. Date: Apr. 5, 2012

(65) Prior Publication Data
US 2013/0197190 A1   Aug. 1, 2013

(30) Foreign Application Priority Data

Oct. 1, 2010 (JP) ................................. 2010-224120

(51) Int. Cl.
C07K 1/14 (2006.01)
C07K 1/30 (2006.01)
C07K 7/06 (2006.01)
C07K 1/36 (2006.01)

(52) U.S. Cl.
CPC . C07K 1/145 (2013.01); C07K 7/06 (2013.01); C07K 1/36 (2013.01)
USPC ............................. 530/329; 530/344; 530/345

(58) Field of Classification Search
None
See application file for complete search history.

(56) References Cited

U.S. PATENT DOCUMENTS

| 3,687,926 | A | * | 8/1972 | Arima et al. ................... 530/329 |
| 5,227,294 | A | | 7/1993 | Carrera et al. |
| 5,264,363 | A | | 11/1993 | Carrera et al. |
| 6,221,637 | B1 | * | 4/2001 | Hida et al. ..................... 435/123 |
| 6,387,687 | B1 | * | 5/2002 | Naotsuka et al. .......... 435/253.5 |
| 7,011,969 | B2 | | 3/2006 | Yoneda et al. |
| 2004/0043451 | A1 | | 3/2004 | Yoneda et al. |
| 2008/0311234 | A1 | | 12/2008 | Yoneda et al. |

FOREIGN PATENT DOCUMENTS

| CN | 101041846 A | 9/2007 |
| JP | 04-299981 A | 10/1992 |
| JP | 2002-176993 A | 6/2002 |
| JP | 2004-027133 A | 1/2004 |
| JP | 2004-067647 A | 3/2004 |
| JP | 2005-272454 A | 10/2005 |
| JP | 2005-306863 A | 11/2005 |
| KR | 10 2004-0055035 A | 6/2004 |
| KR | 20050007670 A | 1/2005 |

OTHER PUBLICATIONS

Arima et al., "Surfactin, a crystalline peptidelipid surfactant produced by *Bacillus subtilis*: isolation, characterization and its inhibition of fibrin clot formation," Biochem. Biophys. Res. Commun., 1996, vol. 31, p. 488-94.
Dimtrov et al., "Liquid Membrane Extraction of Bio-Active Amphilic Substances: Recovery of Surfactin", Biochem. Eng. J., 2008, vol. 42, p. 248-53.
Chen et al., "Recovery and Separation of Surfactin From Pretreated Fermentation Broths by Physical and Chemical Extraction", Biochem. Eng. J., 2008, vol. 38, p. 39-46.
Pryor et al., "Identification of Antifungal Compounds in a Biological Control Product Using a Microplate Inhibition Bioassay", Trans. ASABE, 2006, vol. 49, p. 1643-9.
Yeh et al., "Enhanced Production of Surfactine From *Bacillus subtilis* by Addition of Solid Carriers", Biotechnol. Prog., 2005, vol. 21, p. 1329-34.
Extended European Search Report issued in counterpart European Patent Application No. 11829353.9, dated Feb. 4, 2014.
Kim et al., "Suppression of Inflammatory Responses by Surfactin, a Selective Inhibitor of Platelet Cytosolic Phospholipase $A_2$", Biochemical Pharmacology, vol. 55, Jan. 1, 1998, pp. 975-985.
Lee et al., "PI-003, A Novel Cytosolic Phospholipase $A_2$ Inhibitor Isolated from *Bacillus subtilis*", Korean Biochem J, vol. 26, No. 7, Jan. 1, 1993, pp. 625-631.

* cited by examiner

*Primary Examiner* — Jeffrey E Russel
(74) *Attorney, Agent, or Firm* — Novak Druce Connolly Bove + Quigg LLP

(57) ABSTRACT

The method for producing a surfactin or a salt thereof according to the present invention comprises the steps of adding an organic solvent containing a branched alkyl alcohol to a culture fluid containing the surfactin or the salt thereof, or to a solution obtained by removing an insoluble component from the culture fluid, and extracting the surfactin or the salt thereof with the organic solvent,
wherein the surfactin or the salt thereof is represented by the formula (1):

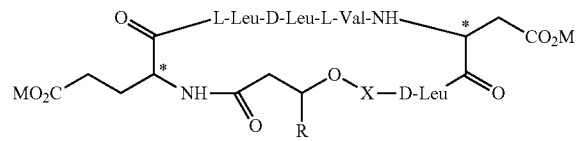

wherein * indicates an optically active center; X is an amino acid selected from leucine, isoleucine and valine; R is a $C_{9-13}$ alkyl group or a $C_{9-13}$ branched alkyl group; and M is an alkali metal, an alkaline earth metal, an optionally-substituted amine or the like.

20 Claims, No Drawings

METHOD FOR PRODUCING SURFACTIN AND SALT THEREOF

CROSS REFERENCE TO RELATED APPLICATIONS

This application is a National Phase filing under 35 U.S.C. §371 of PCT/JP2011/072578 filed on Sep. 30, 2011; and this application claims priority to Application No. 2010-224120 filed in Japan on Oct. 1, 2010, under 35 U.S.C. §119; the entire contents of all are hereby incorporated by reference.

TECHNICAL FIELD

The present invention relates to a method for producing a surfactin or a salt thereof, which has a surfactant property.

BACKGROUND ART

It is reported that a surfactin has various functions such as an antibacterial activity, a hemolyzing property and an activity to inhibit a protein denaturation in addition to a high surfactant property. Therefore, a surfactin is useful as a multifunctional material. It is known that a microorganism belonging to genus *Bacillus* produces a surfactin, and a surfactin can be industrially produced on a large scale by culturing the *Bacillus* microorganism (Patent Document 1 and the like). A method for producing a surfactin and a salt thereof from a culture fluid containing the surfactin is exemplified by:
1) a method in which the culture fluid is acidified, a mixture of methylene chloride:methanol=2:1 by volume is added thereto so as to extract the surfactin in an organic layer, the obtained extract is concentrated, and then the surfactin is purified by thin layer chromatography (TLC) (Patent Document 2);
2) a method in which octane is added to the culture fluid (pH 6), an organic layer is concentrated, and the surfactin is purified with ultrafiltration (Non-Patent Document 1);
3) a method in which an insoluble component such as a fungus body is removed from the culture fluid by centrifugation or the like, the obtained fluid is acidified to obtain a precipitate, methylene chloride is added to the precipitate to extract the surfactin, an organic layer is concentrated, an alkaline aqueous solution is added thereto, an organic layer is discarded, an aqueous layer is acidified to obtain a precipitate, and the precipitate is freeze-dried (Patent Document 3).

PRIOR ART

Patent Document

Patent Document 1: JP 2002-176993 A
Patent Document 2: KR 2005-0007670 A
Patent Document 3: CN 101041846 A

Non-Patent Document

Non-Patent Document 1: Biochemical Engineering Journal, 2008, 42, 248-253

DISCLOSURE OF THE INVENTION

Problems to be Solved by the Invention

However, the above-described production methods, in which a culture fluid is used, are not suitable for an industrial production by the following reasons. For example, the method 1) is not suitable for an industrial production in terms of operability, since methylene chloride to be used as a solvent for extraction causes environmental damage and purification is carried out using thin layer chromatography, though a surfactin can be directly extracted from a culture fluid. The method 2) is not suitable for an industrial production in terms of environmental load and cost, as 2500 parts by weight of a solvent relative to 1 part by weight of a surfactin is needed. In other words, 2.5 ton of a solvent is needed for producing 1 kg of a surfactin. The method 3) is not suitable for an industrial production, since a complicated operation is needed for the method and a solvent which causes environmental damage is used. Specifically, it is necessary that a fungus body is removed, the obtained fluid is acidified to obtain a precipitate, and extraction is carried out from the precipitate using methylene chloride.

Under the above-described circumstance, the objective of the present invention is to provide a method which is economically advantageous and suitable for industrial production for producing a surfactin and a salt thereof without cumbersome procedure. For example, the objective of the present invention is to provide a method for directly extracting a surfactin from a culture fluid without removing an insoluble component such as a fungus body.

In addition to the above objective or as substitute for the above objective, the objective of the present invention is to provide a method for producing a surfactin and a salt thereof to efficiently extract a surfactin from a culture fluid even when an environmental load-reducing solvent is used.

Means for Solving the Problems

The present inventors intensively studied to complete a method for industrially producing a surfactin and a salt thereof. As a result, the inventors found that a surfactin can be easily extracted and purified by using a branched alkyl alcohol as an extraction solvent even when an insoluble component is not removed from a culture fluid.

The present invention relates to a method for producing a surfactin or a salt thereof, characterized in comprising the steps of adding an organic solvent containing a branched alkyl alcohol to a culture fluid containing the surfactin or the salt thereof, or to a solution obtained by removing an insoluble component from the culture fluid, and extracting the surfactin or the salt thereof with the organic solvent,
wherein the surfactin or the salt thereof is represented by the formula (1):

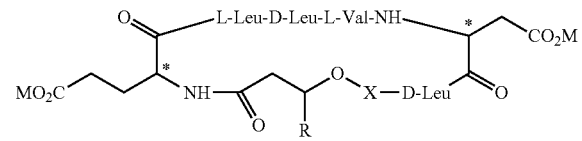

wherein * indicates an optically active center; X is an amino acid selected from leucine, isoleucine and valine; R is a $C_{9-13}$ alkyl group or a $C_{9-13}$ branched alkyl group; and M is an alkali metal, an alkaline earth metal, an optionally-substituted amine or the like.

It is preferred that an aqueous layer during the extraction is acidic and a pH value of the aqueous layer is particularly not less than 1 and not more than 5. A carbon number of the branched alkyl alcohol is exemplified by not less than 3 and not more than 10. It is preferred that a ratio of the branched alkyl alcohol in the organic solvent is not less than 30 wt %. The above-described organic solvent may further contain an auxiliary solvent, and it is recommended that a total ratio of the branched alkyl alcohol and the auxiliary solvent is not less than 0.6 parts by weight and not more than 1.5 parts by weight relative to 1 part by weight of the culture fluid.

The extraction fluid may be mixed with a basic aqueous solution, and then an organic layer may be removed to obtain an aqueous solution. Next, the aqueous solution may be mixed with an inorganic acid. As a result, the surfactin can be precipitated in a solid form from the mixture. In addition, the extraction fluid may be mixed with a base so as to obtain the surfactin salt in a solid form from the mixture. In order to obtain the surfactin salt or a solution thereof, the surfactin obtained by the above-described production method may be mixed with a base.

Effect of the Invention

By the present invention method, a surfactin and a salt thereof can be purified efficiently and economically-advantageously without a cumbersome operation. In addition, a branched alkyl alcohol which is used for extraction is environmentally-friendly. Therefore, the present invention method can be preferably applied to an industrial production.

MODE FOR CARRYING OUT THE INVENTION

Hereinafter, the present invention is described in detail.

In the present invention, a branched alkyl alcohol is used for extracting a surfactin or a salt thereof from a culture fluid.

A surfactin or a salt thereof which is extracted from a culture fluid is represented by the following formula (1):

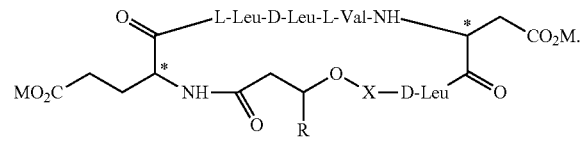

Hereinafter, the above surfactin or the salt thereof is referred to as "compound (1)". The meaning of the abbreviations in the formula is described as follows:

L-Leu: L-leucine
D-Leu: D-leucine
L-Val: L-valine.

In the formula (1), * indicates an optically active center.

X is an amino acid selected from leucine, isoleucine and valine.

R is a $C_{9-13}$ linear alkyl group or a $C_{9-13}$ branched alkyl group. Such a $C_{9-13}$ linear alkyl group is exemplified by a nonyl group, a decyl group, an undecyl group, a dodecyl group, tridecyl group and the like. The $C_{9-13}$ branched alkyl group is exemplified by a 7-methyloctyl group, an 8-methylnonyl group, a 9-methyldesyl group, a 10-methylundecyl group, an 11-methyldodecyl group, a 6-methyloctyl group, a 7-methylnonyl group, an 8-methyldesyl group, a 9-methylundecyl group, a 10-methyldodecyl group and the like. The above-described groups may be substituted with one substituent or not less than 2 substituents. Such a substituent is exemplified by an amino group, a hydroxy group, a phenyl group, an aryl group, an alkanoyl group, an alkenyl group, an alkynyl group, an alkoxy group, a nitro group, a halogen atom and the like.

M is a hydrogen, an alkali metal, an alkaline earth metal, an optionally-substituted amine or the like. In the optionally-substituted amine, an optionally-substituted ammonium is included. The alkali metal is not particularly limited, and is lithium, sodium, potassium or the like. The alkaline earth metal is not particularly limited, and is beryllium, magnesium, calcium or the like. The optionally-substituted amine is not particularly limited as long as the amine can form a salt with a surfactin, and is a mono-substituted amine ($RNH_3$), a di-substituted amine and tri-substituted amine in addition to ammonia. The substituent of the amine is exemplified by an alkyl group such as a methyl group, an ethyl group, a n-propyl group, an isopropyl group, a n-butyl group and a tert-butyl group; an aralkyl group such as a benzyl group, a methylbenzyl group and a phenylethyl group; and an aryl group such as a phenyl group, a toluoyl group and a xylyl group; and the like. Specifically, the amine is exemplified by methylamine, ethylamine, benzylamine, aniline, diethylamine, dicyclohexylamine, pyrrolidine, morpholine, N-benzyl-N-ethylamine, N-ethylaniline, triethylamine, pyridine and the like. A proton may be added to the amine to become an ammonium ion. The above-described organic groups may be substituted with one substituent or not less than 2 substituents.

M is preferably an alkali metal such as sodium and potassium, and particularly sodium.

A surfactin is contained in a culture fluid of a microorganism. For example, such a culture fluid can be preferably prepared with the method described in JP 2002-176993 A. More specifically, the microorganism to be used is exemplified by a microorganism belonging to genus *Bacillus*, preferably *Bacillus subtilis*, and more preferably *Bacillus subtilis* SD901 of which international deposit number is FERM BP-7666.

In general, the above-described microorganism is preliminarily cultured to increase the number of the microorganism in a nutritive medium, and then cultured by transferring the preliminarily-culture fluid to a main culture fluid. The nutritive medium is exemplified by L medium consisting of 1 wt/v % polypeptone, 0.5 wt/v % yeast extract, 0.5 w/v % NaCl and the remnant of water. In the above preliminarily-culture, an appropriate dose of an antibiotic such as chloramphenicol and tetracycline may be added if necessary to inhibit the growth of other microorganism. For example, not less than 1 ppm and not more than 30 ppm by mass of an antibiotic may be added. Hereinafter, the unit "ppm" is based on mass.

The main culture fluid generally contains a carbon source, a nitrogen source, a metal ion and a pH adjuster. Such a carbon source is exemplified by a sugar such as glucose, maltose and sucrose; a starch; an alcohol; an organic acid; and the like. For example, an amount of a carbon source in the main culture fluid may be adjusted to be not less than about 1% by mass and not more than about 40% by mass.

The nitrogen source is exemplified by a soy powder or an extract therefrom, an ammonium salt, a nitrate, peptone, a meat extract, a yeast extract and the like. A soy powder or an extract therefrom may be used singly or in combination with other nitrogen source such as a yeast extract. For example, an amount of a nitrogen source may be adjusted to be not less than about 0.1% by mass and not more than about 20% by mass. When a soy powder or an extract therefrom is used in combination with a yeast extract, for example, a ratio of the soy powder or the extract therefrom may be adjusted to be not less than about 0.1% by mass and not more than about 20% by mass and a ratio of the yeast extract may be adjusted to be not less than about 0.001% by mass and not more than about 1% by mass.

The metal ion, i.e. mineral, is exemplified by a magnesium ion, an iron ion, a manganese ion, a calcium ion, a zinc ion, a cobalt ion, a nickel ion, a copper ion, a molybdenum ion and the like. In general, two or more metal ions are used in combination and added in a form of metal salts. The salt is exemplified by a sulfate, a chloride salt, a phosphate and the like. For example, an amount of the metal salt may be adjusted to be not less than about 10 ppm and not more than about 1000 ppm. In the metal ion, an alkali metal ion such as a potassium ion and a sodium ion is included. However, when an amount of the metal ion is determined, such an alkali metal ion is not included in the metal ion, since the alkali metal ion may be added in large amount as a pH adjuster.

As the pH adjuster, a phosphate, such as sodium phosphate and potassium phosphate, or the like is used. For example, an amount of the pH adjuster is not less than about 0.1% by mass and not more than about 10% by mass.

To the above-described main culture fluid, an amino acid such as L-tryptophan and L-arginine may be added in an appropriate amount (for example, not more than 1 w/w %) as necessary. In addition, a vitamin may be added in an appropriate amount (for example, not more than 100 ppm).

A temperature of the preliminary culture and the main culture is exemplified by not less than 25° C. and not more than 42° C. A concentration of a surfactin after the main culture is exemplified by not less than about 1% by mass and not more than about 10% by mass.

In the most preferable condition, for example, *Bacillus subtilis* SD901 (FERM BP-7666) is cultured in a nutritive medium containing 10 ppm of tetracycline in a temperature condition of not less than 25° C. and not more than 42° C. for not less than about 5 hours and not more than about 24 hours. To a medium containing a soy powder or an extract therefrom as a nitrogen source, the obtained culture fluid is added in a concentration of not less than 0.1 wt % and not more than 10 wt %. A surfactin can be preferably obtained by incubating the medium at a temperature of not less than 25° C. and not more than 42° C. for not less than 20 hours and not more than 90 hours.

In the present invention, a branched alkyl alcohol is used as an extraction solvent, and thereby a surfactin can be easily extracted without removing an insoluble component from a culture fluid. However, if necessary, an insoluble component may be removed from a culture fluid. For example, an insoluble component which generates during a culture may be removed by a conventional means such as centrifugation, pressure filtration and filter press.

Next, an extraction procedure is described with examples. However, an extraction method is not particularly limited, and any extraction methods are included in the range of the present invention as long as a branched alkyl alcohol is used as an extraction solvent.

To a culture fluid containing a surfactin or a salt thereof, an organic solvent containing a branched alkyl alcohol is added. If necessary, the mixture is acidified by further adding an acid. The mixture is stirred for a predetermined time. Then, the mixture is settled and an aqueous layer is discarded. An order of adding a culture fluid and an organic solvent containing a branched alkyl alcohol is not particularly limited, and a culture fluid may be added to an organic solvent containing a branched alkyl alcohol. In addition, a branched alkyl alcohol and other solvent may be respectively added.

A carbon number of the alkyl part of a branched alkyl alcohol to be used is exemplified by not less than 3 and not more than 10, preferably not less than 3 and not more than 6, and more preferably not less than 3 and not more than 5. The carbon at the branched point may be a secondary carbon or a tertiary carbon, and preferably a tertiary carbon. The number of the branched point, i.e. the number of secondary carbon and tertiary carbon, is exemplified by not less than about 1 and not more than about 3, preferably not less than about 1 and not more than about 2, and particularly 1. Specifically, such a branched alkyl alcohol is exemplified by isopropyl alcohol, isobutyl alcohol, sec-butyl alcohol, t-butyl alcohol, neopentyl alcohol, t-pentyl alcohol, isohexyl alcohol, 5-methylhexyl alcohol, 6-methylheptyl alcohol, 7-methyloctyl alcohol and the like. The above-described alkyl group may not be substituted and may be substituted. Such a substituent is exemplified by an amino group, a hydroxy group, a phenyl group, an aryl group, an alkanoyl group, an alkenyl group, an alkynyl group, an alkoxy group, a nitro group, a halogen atom and the like. The alcohol is particularly preferably isopropyl alcohol, isobutyl alcohol and tert-butyl alcohol. A surfactin and a salt thereof can be easily extracted using a branched alkyl alcohol.

As an organic solvent used as an extraction solvent, an auxiliary solvent may be further used in addition to a branched alkyl alcohol.

An auxiliary solvent to be used is exemplified by a hydrocarbon solvent, an ester solvent, an ether solvent, a ketone solvent, a nitrile solvent and the like. A hydrocarbon solvent is exemplified by toluene, benzene, xylene, hexane, cyclohexane, heptane and the like. An ester solvent is exemplified by methyl acetate, ethyl acetate, propyl acetate, methyl propionate, ethyl propionate and the like. An ether solvent is exemplified by diethyl ether, diisopropylether, tetrahydrofuran, 1,4-dioxane and the like. A ketone solvent is exemplified by acetone, methyl ethyl ketone and the like. A nitrile solvent is exemplified by acetonitrile, propionitrile and the like. An auxiliary solvent is preferably toluene, ethyl acetate, tetrahydrofuran, acetone and acetonitrile.

A ratio of a branched alkyl alcohol and an auxiliary solvent affects a separating speed, and is adjusted depending on the kind of a branched alkyl alcohol and a combination of a branched alkyl alcohol with an auxiliary solvent.

For example, in a case of an alcohol such as t-butyl alcohol of which branched point is a tertiary carbon, even when such an alcohol is used singly without an auxiliary solvent, the mixture can be separated; but, an auxiliary solvent may be also used in combination. On the other hand, in a case of an alcohol such as isopropyl alcohol of which branched point is a secondary carbon, particularly of which carbon number is not more than 4, the mixture containing a culture fluid may be hardly separated; therefore, an organic layer is preferably diluted with an auxiliary solvent. When an alcohol of which branched point is a secondary carbon is used in combination with an auxiliary solvent (for example, an ester solvent such as ethyl acetate), it is preferred that a ratio of an alcohol of which branched point is a secondary carbon, such as isopropanol, in an organic solvent is adjusted to be, for example, not more than 90 wt %, and preferably not more than 80 wt %.

When an auxiliary solvent is used, in order to separate the mixture appropriately, a ratio of a branched alkyl alcohol in an organic solvent is adjusted to be, for example, not less than 10 wt % and not more than 90 wt %, preferably not less than 20 wt % and not more than 80 wt %, more preferably not less than 30 wt % and not more than 80 wt %, and particularly not less than 45 wt % and not more than 60 wt %.

An amount of an extraction solvent, i.e. an organic solvent, may be adjusted according to the kind of the solvent to be used. When the amount is too small, a separating speed may possibly become low and efficiency may be decreased. On the other hand, too large amount is economically disadvantaged. An appropriate amount relative to 1 part by weight of a culture fluid is, for example, not less than 0.2 parts by weight and not more than 2.5 parts by weight, preferably not less than 0.4 parts by weight and not more than 2.0 parts by weight, and more preferably not less than 0.6 parts by weight and not more than 1.5 parts by weight.

With respect to an acidic condition when an acid is added to a culture fluid, in general, the value of pH may be preferably adjusted to be less than 7. As a result, an extraction may be successfully carried out. On the other hand, when the value of pH is more than 5, much an amount of a solvent may be needed or an extraction times may be increased since an extraction rate may be lowered. As a result, a procedure may become cumbersome, and industrial and economical disadvantage may be created. Therefore, when the value of pH is more than 5, it is preferred that the value of pH is adjusted using a acid. The value of pH may be adjusted to be not more than 4.

On the other hand, when the value of pH is too low, a limitation may be created in terms of a facility though there is no problem in terms of a yield. The value of pH is preferably not less than about 1, for example, not less than 3.

An acid to be used is not particularly limited, and is exemplified by an inorganic acid such as hydrochloric acid, sulfuric acid, nitric acid and phosphoric acid; and an organic acid such as formic acid, acetic acid and propionic acid.

A temperature for separating the mixture is not particularly limited as long as a culture fluid is not solidified nor evaporated, and the separation can be successfully carried out generally at not less than 0° C. and not more than 80° C., preferably not less than 0° C. and not more than 60° C., and particularly not less than 0° C. and not more than 40° C.

When a surfactin or a salt thereof is extracted under the above-described preferable condition, in general, a separating speed becomes preferred industrially. When a speed for completely separating the mixture into an upper layer and a lower layer is represented as a depth of an organic layer/a separating time, in general, such a speed is preferably not less than 0.01 cm/min, and more preferably not less than 0.05 cm/min. If a condition is appropriately selected, the mixture can be separated at a speed of not less than 0.10 cm/min, for example, not less than 0.5 cm/min, and further not less than 1 cm/min.

If a solvent, the value of pH and the like are selected as described above, the compound (1) as an acid form, in which M is a hydrogen, can be efficiently obtained from an organic layer.

When an extraction is carried out under the above-described preferable condition, a yield per one time extraction is generally not less than 60 mol %. If a ratio of a branched alkyl alcohol and an amount of a solvent are adjusted, the objective compound can be recovered in a yield of not less than 90 mol %.

The extract, i.e. the organic layer, obtained as the above may be directly concentrated and dried to isolate a surfactin. Alternatively, a surfactin salt may be precipitated as a solid by adding a base and drying. When a surfactin salt is not precipitated as a solid, the solution may be concentrated and dried. The extract may be treated with an activated carbon as necessary, and then the above procedure may be carried out.

A base used for forming a surfactin salt is not particularly limited, and is exemplified by an alkali metal such as lithium, sodium and potassium; an alkaline earth metal such as beryllium, magnesium and calcium. Specifically, sodium hydroxide, potassium hydroxide and the like are exemplified. The following type of an amine base, in which an optionally-substituted ammonium is included, in addition to ammonia may be used. In the present invention, an amine means a mono-substituted amine, a di-substituted amine or a tri-substituted amine. A substituent of an amine is exemplified by an alkyl group such as a methyl group, an ethyl group, a n-propyl group, an isopropyl group, a n-butyl group and a tert-butyl group; an aralkyl group such as a benzyl group, a methylbenzyl group and a phenylethyl group; and an aryl group such as a phenyl group, a toluoyl group and a xylyl group. Specifically, an amine is exemplified by methylamine, ethylamine, benzylamine, aniline, diethylamine, dicyclohexylamine, pyrrolidine, morpholine, N-benzyl-N-ethylamine, N-ethylaniline, triethylamine, pyridine and the like. The above amine may be further protonated to become an ammonium ion. The above organic group may be further substituted with one substituent or not less than 2 of substituents.

An amount of a base is not particularly limited as long as the base can form a salt with a surfactin, and is generally not less than 0.5 times by mole and not more than 4 times by mole relative to a surfactin.

A surfactin and a salt thereof can be further purified from the extract which is obtained as the above and the concentrate thereof by changing the solubility of the surfactin in a wash solution to remove an impurity. In other words, the extract or the concentrate thereof is mixed with an aqueous solution of a base to change the compound (1) into a water-soluble salt, and an organic layer is removed to obtain an aqueous solution of a surfactin salt. Then, the aqueous solution is mixed with an acid to be acidified. As a result, an acid form of the compound (1), of which M is a hydrogen, can be precipitated from the solution as a solid.

A method for mixing the extract, water and a base is not particularly limited. Water may be added to the extract or the concentrate and then a base may be added thereto; the extract or the concentrate may be mixed with an aqueous solution containing a predetermined amount of a base; or the extract or the concentrate may be finally added to be mixed.

A base to be used in the present invention is not particularly limited, and is exemplified by an alkali metal such as lithium, sodium and potassium; and an alkaline earth metal such as beryllium, magnesium and calcium. As a base, an organic base such as triethylamine in addition to ammonia may be used. A base is preferably an alkali metal salt such as sodium hydroxide and potassium hydroxide.

An amount of a base can be adjusted insofar as the compound (1) can be dissolved in an aqueous layer, and not less than 0.5 times by mole and not more than 4 times by mole of a base relative to the compound (1) is generally used.

An acid which is used for precipitating the acid form from an aqueous solution is not particularly limited, and is exemplified an inorganic acid such as hydrochloric acid, sulfuric acid, nitric acid and phosphoric acid; an organic acid such as formic acid, acetic acid and propionic acid; and the like. The acid is preferably an inorganic acid such as hydrochloric acid and sulfuric acid.

When an aqueous solution of a surfactin salt is mixed with an acid, an aqueous solution of a surfactin salt may be added to an acidic aqueous solution which is preliminarily prepared or an acid may be added to an aqueous solution of a surfactin. From the view of handleability, it is preferable that an aqueous solution of a surfactin salt is added to an acidic solution, of which viscosity at the time of neutralization is lower.

A temperature at the time of mixing is not particularly limited as long as a surfactin is not decomposed, and is generally not less than 0° C. and not more than 80° C., preferably not less than 0° C. and not more than 60° C., and more preferably not less than 0° C. and not more than 40° C.

After an aqueous solution of a surfactin salt is mixed with an acid, the mixture is settled for a while to be matured.

A temperature at the time of maturing can be preferably adjusted in the same range when the above-described acid is mixed.

A solid of the precipitated surfactin can be separated to be isolated by a conventional means such as centrifugation and pressure filtration.

The thus obtained surfactin may be further mixed with a base in an aqueous solution or an organic solvent in order to obtain a surfactin salt. Such a surfactin salt can be obtained as a solid by concentrating and drying the mixture, if necessary. In addition, a highly pure surfactin salt can be obtained by treating the mixture with an activated carbon before drying as necessary.

A base to be used is exemplified by the above-described bases for forming a surfactin salt.

An amount of a base is not particularly limited as long as the base can form a salt with a surfactin, and is preferably not less than 0.5 times by mole and not more than 4 times by mole relative to the surfactin.

A method for drying the obtained solid is not particularly limited, and a conventional drying method such as spray-dry method and freeze-dry method can be preferably carried out.

It is possible by the above-described method that not less than 35 g of a surfactin or a salt thereof can be obtained per 1 kg of a culture fluid.

EXAMPLES

Hereinafter, the present invention is specifically described with Examples. However, the present invention is not limited to the Examples.

In the following Examples, a culture fluid prepared as the following procedure was used.

*Bacillus subtilis* SD901 (FERM BP-7666) was linearly inoculated on a L plate medium which contained 10 ppm of tetracycline and grown at 35° C. overnight. In a flask having a baffle, 100 ml of a L medium which contained 10 ppm of tetracycline was prepared. A loopful grown bacteria was inoculated on the medium using a platinum loop and cultured at 35° C. and at 150 rpm for 12 hours. In a fermenter having a 5 L capacity, 2 L of a medium having the following composition was prepared. The L fluid medium was added to the prepared medium, and culture was carried out at 35° C. with adjusting the pH to be 6.5 to 7.5 using 20% NaOH. When the objective concentration of a surfactin sodium salt was achieved, the cultivation was terminated.

| Medium Composition (w/w %) | |
|---|---|
| Soy powder | 10% |
| $K_2HPO_4$ | 0.5% |
| $MgSO_4 \cdot 7H_2O$ | 0.05% |
| $FeSO_4 \cdot 7H_2O$ | 25 ppm |
| $MnCl_2 \cdot 4H_2O$ | 22 ppm |
| Yeast extract | 0.1% |
| Maltose | 17% |
| L-Tryptophan | 0.1% |
| L-Arginine | 0.1% |

Example 1

To 600 g of the above culture fluid which contained 34 g of a surfactin sodium salt, 264 g of isopropanol and 198 g of ethyl acetate was added. The ratio by mass of the organic solvents/the culture fluid was 0.77, the ratio by mass of isopropanol/the culture fluid was 0.44, and the isopropanol concentration in the organic solvents was 57 mass %. The pH was adjusted to be 3.8 by adding 15 g of 55% sulfuric acid at 25° C. After the mixture was settled for 8 minutes, an aqueous solution was discarded to obtain 573 g of an organic layer, i.e. an extract, in which 31 g of a surfactin was included (extraction yield: 91 mol %). The depth of the organic layer was 6.4 cm and the separating time was 8 minutes. The separating speed was calculated from the data to be 0.8 cm/min.

Example 2

To 20 g of a culture fluid which contained 0.9 g of a surfactin, isopropanol and ethyl acetate of the amount described in Table 1 were added. The pH of the mixture was adjusted to be 4 using 55% sulfuric acid, and then the separating speeds in each condition were compared.

The separating speed was calculated from the depth of the organic layer after the mixture was completely separated and the time required for the complete separation of the mixture. As the following results, it was found that when the ratio of isopropanol in the extraction solvent is high, a separating speed becomes fast.

TABLE 1

| | Run 1 | Run 2 | Run 3 | Run 4 | Run 5 | Run 6 | Run 7 |
|---|---|---|---|---|---|---|---|
| Isopropanol | 8.4 g | 8.8 g | 9.6 g | 7.8 g | 8.4 g | 8.8 g | 7.2 g |
| Ethyl acetate | 8 g | 8 g | 8 g | 7 g | 7 g | 7 g | 6 g |
| Separating speed (cm/minute) | <0.03 | 0.06 | 2.4 | <0.03 | 0.13 | 0.29 | <0.03 |

Example 3

To 30 g of a culture fluid which contained 0.9 g of a surfactin, 5 g of the solvent described in described Table 2 was added. The mixture was vigorously stirred. Then, the mixture was settled for 2 days, and it was observed whether the mixture was separated or not. As a result, when a higher alcohol of which alkyl group was branched was used, the separating speed was faster.

TABLE 2

| Solvent | Separating property |
|---|---|
| n-Butanol | Not bad |
| iso-Butanol | Not bad |
| tert-Butanol | Excellent |

Excellent: the mixture was separated well.

Not bad: an emulsion part remained, and the mixture was difficult to be separated.

Example 4

To 21 g of a surfactin extract which contained 5 g of a surfactin and which was obtained under the same condition as the Example 1, 5 g of an activated carbon was added. The mixture was stirred for 17 hours. The activated carbon was removed by filtration, and the obtained filtrate was concentrated under reduced pressure. After hexane was added to the residue, the mixture was concentrated under reduced pressure. The treatment was repeated once more. Then, the residue was dried in vacuo to obtain 4.8 g of a surfactin.

Example 5

To 21 g of a surfactin extract which contained 5 g of a surfactin and which was obtained under the same condition as the Example 1, 5 g of an activated carbon was added. The mixture was stirred for 17 hours. The activated carbon was removed by filtration. The pH of the obtained filtrate was adjusted to be 7 using 30% sodium hydroxide. Then, the mixture was concentrated under reduced pressure. After hexane was added to the residue, the mixture was concentrated under reduced pressure. The treatment was repeated once more. Then, the residue was dried in vacuo to obtain 5.6 g of a surfactin sodium salt as a solid.

Example 6

To 726 g of a culture fluid obtained under the same condition as the Example 1, 290 g of isopropanol and 290 g of ethyl acetate were added. The pH of the mixture was adjusted to be 4 using 47% sulfuric acid. After the mixture was settled for 3 hours, the mixture was separated into an organic layer and an aqueous layer, to obtain 532 g of the first upper layer (the organic layer), which contained water. Then, 145 g of isopropanol and 145 g of ethyl acetate were added to the lower layer (the aqueous layer) to be mixed, and the mixture was settled for 1 hour to obtain 545 g of the second upper layer (the organic layer), which contained water. The first upper layer and the second upper layer were mixed, and then the mixture, which contained a 39 g of a surfactin, was concentrated under reduced pressure until the amount of the residue became 378 g. After 96 g of ethyl acetate was added to the concentrate, an aqueous layer was removed. The obtained organic layer was filtrated, and 39 g of an activated carbon was added to the obtained filtrate. The mixture was stirred for 14 hours. The activated carbon was removed by filtration and washed with 55 g of ethyl acetate. To the obtained filtrate, 83 g of water and 7 g of 30% sodium hydroxide aqueous solution were added. Then, an organic layer was removed, and the obtained aqueous layer was concentrated under reduced pressure until the amount became 143 g. The thus obtained aqueous solution was added dropwise to 117 g of 2% sulfuric acid at 13° C. over 3 hours. The obtained slurry was matured for 13 hours, and the solid component was removed by filtration and washed with water to obtain 92 g of a surfactin wet solid which contained 28 g of a pure surfactin. To 92 g of the solid, 108 g of water was added. The pH of the mixture was adjusted to be 7 using 30% sodium hydroxide aqueous solution, and 9 g of an activated carbon was added thereto. The mixture was matured for 14 hours. After the activated carbon was removed by filtration, the obtained filtrate was freeze-dried to obtain 27 g of a solid surfactin sodium salt as a solid.

INDUSTRIAL APPLICABILITY

The present invention is useful for producing a surfactin or a salt thereof, since an extraction efficiency from a culture fluid can be improved by the present invention. A surfactin has various functions such as antibacterial activity, a hemolyzing property and an activity inhibit a protein denaturation in addition to a surfactant property. Therefore, the present invention is industrially very useful.

The invention claimed is:

1. A method for producing a surfactin or a salt thereof, comprising the steps of adding an organic solvent containing a branched alkyl alcohol and an auxiliary solvent to a culture fluid containing the surfactin or the salt thereof, or to a solution obtained by removing an insoluble component from the culture fluid, and extracting the surfactin or the salt thereof with the organic solvent,
wherein a total ratio of the branched alkyl alcohol and the auxiliary solvent is not less than 0.6 parts by weight and not more than 1.5 parts by weight relative to 1 part by weight of the culture fluid, and
the surfactin or the salt thereof is represented by the formula (1):

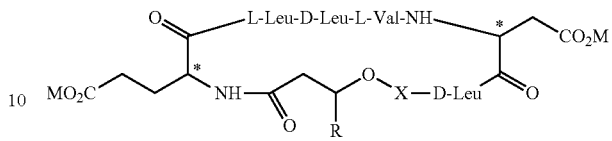

wherein * indicates an optically active center; X is an amino acid selected from leucine, isoleucine and valine; R is a $C_{9-13}$ linear alkyl group or a $C_{9-13}$ branched alkyl group; and M is a hydrogen, an alkali metal, an alkaline earth metal, or an optionally-substituted amine.

2. The method according to claim 1, wherein an aqueous layer during the extraction is acidic.

3. The method according to claim 2, wherein a pH value of the aqueous layer during the extraction is not less than 1 and not more than 5.

4. The method according to claim 1, wherein a carbon number of the branched alkyl alcohol is not less than 3 and not more than 10.

5. The method according to claim 1, wherein a concentration of the branched alkyl alcohol in the organic solvent is not less than 30 wt %.

6. The method according to claim 1, further comprising the steps of:
  a) obtaining an aqueous solution containing the surfactin salt by mixing the extract containing the surfactin with a basic aqueous solution and then removing an organic layer; and
  b) mixing the aqueous solution containing the surfactin salt with an inorganic acid to precipitate the surfactin in a solid form from the obtained mixture.

7. The method according to claim 1 further comprising the step of mixing the extract containing the surfactin with a base to obtain the surfactin salt obtained in a solid form from the obtained mixture.

8. The method according to claim 1, further comprising the step of mixing the surfactin after the extracting with a base in an aqueous solution or an organic solvent in order to obtain a surfactin salt.

9. The method according to claim 2, further comprising the steps of:
  a) obtaining an aqueous solution containing the surfactin salt by mixing the extract containing the surfactin with a basic aqueous solution and then removing an organic layer; and
  b) mixing the aqueous solution containing the surfactin salt with an inorganic acid to precipitate the surfactin in a solid form from the obtained mixture.

10. The method according to claim 2, further comprising the step of mixing the extract containing the surfactin with a base to obtain the surfactin salt in a solid form from the obtained mixture.

11. The method according to claim 2, further comprising the step of mixing the surfactin after the extracting with a base in an aqueous solution or an organic solvent in order to obtain a surfactin salt.

12. The method according to claim 4, further comprising the step of mixing the surfactin after the extracting with a base in an aqueous solution or an organic solvent in order to obtain a surfactin salt.

13. The method according to claim 2, wherein a carbon number of the branched alkyl alcohol is not less than 3 and not more than 10.

14. The method according to claim 3, wherein a carbon number of the branched alkyl alcohol is not less than 3 and not more than 10.

15. The method according to claim 2, wherein a concentration of the branched alkyl alcohol in the organic solvent is not less than 30 wt %.

16. The method according to claim 3, wherein a concentration of the branched alkyl alcohol in the organic solvent is not less than 30 wt %.

17. The method according to claim 4, wherein a concentration of the branched alkyl alcohol in the organic solvent is not less than 30 wt %.

18. The method according to claim 3, further comprising the step of mixing the extract containing the surfactin with a base to obtain the surfactin salt in a solid form from the obtained mixture.

19. The method according to claim 4, further comprising the step of mixing the extract containing the surfactin with a base to obtain the surfactin salt in a solid form from the obtained mixture.

20. The method according to claim 5, further comprising the step of mixing the extract containing the surfactin with a base to obtain the surfactin salt in a solid form from the obtained mixture.

* * * * *